! USOO5328991A

United States Patent [19]
Kuo

[11] Patent Number: 5,328,991
[45] Date of Patent: Jul. 12, 1994

[54] PREPARATION OF ALKALI-MODIFIED CAT DANDER ALLERGEN (FEL D I) FOR IMMUNOTHERAPEUTIC PURPOSES

[75] Inventor: Mei-chang Kuo, Winchester, Mass.

[73] Assignee: Immulogic Pharmaceutical Corp., Waltham, Mass.

[21] Appl. No.: 662,193

[22] Filed: Feb. 28, 1991

Related U.S. Application Data

[63] Continuation-in-part of Ser. No. 431,565, filed as PCT/US90/06548, Jan. 2, 1990, abandoned.

[51] Int. Cl.$^5$ .................. A61K 39/35; A61K 37/02; C07K 13/00; C12P 21/02
[52] U.S. Cl. .................. 530/403; 530/405; 530/406; 530/402; 530/350; 424/185.1; 424/276.1
[58] Field of Search .............. 435/68.1, 69.2, 272; 530/413, 304, 405, 406; 424/88, 91; 514/8

[56] References Cited

U.S. PATENT DOCUMENTS 4,163,778  8/1979  Ohman .................. 424/91
4,946,945  8/1990  Wojdani ................ 530/402

FOREIGN PATENT DOCUMENTS 038153  10/1981  European Pat. Off. .
367306  5/1989   European Pat. Off. .
82-01132 4/1982  World Int. Prop. O. .

OTHER PUBLICATIONS

Kudo, K., et al. (1976) J. Allergy Clin. Immunol. 61:1-9.
Oka, S. et al. (1987) J. Allergy Clin. Immunol. 80:57-63.
Didierlaurent, A. et al., Int. Archs. Allergy Appl. Immun., vol. 73:27-31 (1984).
Jenkins, M. et al., J. Exp. Med., vol. 165: 302-319 (1987).
DeGroot, H. et al., J. Allergy Clin. Immunol., vol. 82: 778-786 (1988).
Chapman, M. et al., J. Of Immun, vol. 140(3): 812-818 (Feb. 1, 1988).
Duffort, O. et al., Immunology Letters, vol. 17: 71-77 (1988).
Duffort, O. et al., Int. Archs. Allergy appl. Immun., vol. 84: 339-344 (1987).
Sundin, B., et al., J. of Allergy Clin. Immunol., vol. 77: 478-487 (1986).
Lowenstein, H. et al., Allergy, vol. 40: 430-441 (1985).
Anderson, M. et al., J. Allergy Clin. Immunol., vol. 76: 563-569 (1985).
Ohman, J. et al., J. Allergy Clin. Immunol., vol. 4: 230-239 (1984).
Leitermann, K. et al., J. Allergy Clin. Immunol., vol. 74: 147-153 (1984).
Ohman, J. et al, J. Of Immunology, vol. 113 (6): 1668-1677 (Dec. 1974).
Barnes et al., J. Allergy & Clinical Immunology, vol. 85: 169 (1990).
Lerner, Richard A., "Tapping the immunological repertoire to produce antibodies of predetermined specificity", Nature, vol. 299, Oct. 14, 1982.
Morgenstern, Jay et al., Proc. Natl. Acad. Sci. USA, vol. 88, Nov. 1991, pp. 9690-9694.

Primary Examiner—Robert J. Hill, Jr.
Assistant Examiner—David L. Fitzgerald
Attorney, Agent, or Firm—Stacey L. Channing; Leon R. Yankwich; Darlene A. Vanstone

[57] ABSTRACT

Proteins, referred to as modified human T cell reactive feline proteins, which have reduced ability to bind immunoglobulin E from cat allergic individuals and substantially unaltered ability to stimulate T cells from cat allergic individuals (relative to affinity purified T cell reactive feline protein) and a method of making such proteins. The modified human T cell reactive feline proteins are useful in desensitization treatment of cat allergic individuals.

11 Claims, 6 Drawing Sheets

```
                                                      -20
C1 Leader A                               C I M K G A R V L V L L W A A L L L I W G G N C
                                                                     -10
C1 Leader B                       A W R C S W K R M L D A A L P P C P T B A A T A D C
                        5              10              15             20             25             30              35
C1          E I C P A V K R D V D L F L T G T P D E Y V E Q V A Q Y K A L P V V L
PRO.        - - - - - - - - - - - - - - - - - - - - - - - - - - - - - - - - - - -
                  40             45             50             55             60             65              70
C1          E N A R I L K N C V D A K M T E E D K E N A L S L L D K I Y T S P L C
PRO.        - - - - - - - - - - - - - - - - - - - - - - - - - - - - - - - - - - -
```

TRFP CHAIN #1 PROTEIN SEQUENCE

Fig. 1a

```
C2 Leader                     DTMRGALLVLALLVTQALG
                                           -10
                 5         10        15        20        25        30        35        40
C2L     V K M A E T C P I F Y D V F F A V A N G N E L L L D L S L T K V N A T E P E R T
C2S     - - - - - - - - - - - - - - - - - - - - - - - - - - - - - - - - - - - - - - -
C2ST    - - - - - - - - - - - - - - - - - - - - - - - - - - - - - - - - - - - - - - -
PRO.    - - - - - - - - - - - - - - - - - - - - - - - - - - - - - - - X - - - - - - -

45        50        55        60        65        70        75        80
C2L     A M K K I Q D C Y V E N G L I S R V L D G L V M T T I S S S K D C M G E A V Q N
C2S     - - - - - - - - - - - - - - - - - - - - - - - - - I A - N E * * Y - - - - - - -
C2ST    - - - - - - - - - - - - - - - - - - - - - - - - - - P S T N I A W V K Q F R T P
PRO.    - - - - - - - - - - - - - - - - - - - - - - - T T - S S ( - - - K ) - - - - - -
                                                      I A - N E

85        90
C2L     T V E D L K L N T L G R
C2S     - - - - - - - - - - - -
PRO.    T V -
        A M
```

TRFP CHAIN #2 PROTEIN SEQUENCES

ANTIGENS

A - TRFP

B - KOH - TREATED TRFP

ANTIBODIES

1 - MONOCLONAL MIX

2 - POOLED HUMAN PLASMA

3 - ANTI-PEPTIDE ANTISERA

PREPARATION OF ALKALI-MODIFIED CAT DANDER ALLERGEN (FEL D I) FOR IMMUNOTHERAPEUTIC PURPOSES

RELATED APPLICATIONS

The present application is a continuation-in-part of U.S. application Ser. No. 07/431,565, filed Nov. 3, 1989 and now abandoned.

This application also claims priority to International Application No. PCT/US90/06548, filed Nov. 2, 1990. This application is also related to and incorporates by reference the teachings of commonly assigned, copending U.S. application Ser. No. 07/662,276, filed Feb. 28, 1991.

BACKGROUND

Genetically predisposed individuals, who make up about 10% of the population, become hypersensitized (allergic) to antigens from a variety of environmental sources to which they are exposed. Those antigens that can induce immediate and/or delayed types of hypersensitivity in people are called allergens. King, T. P., *Adv. Immun.* 23:77–105(1976). The symptoms of hay fever, asthma and hives are forms of allergy which can be caused by a variety of allergens, such as products of grasses, trees, weeds, animal dander, insects, food, drugs and chemicals. The antibodies involved in allergy belong primarily to the immunoglobulin E (IgE) class of immunoglobins. IgE binds to mast cells and basophils. Upon combination of a specific allergen with IgE bound to mast cells, the IgE is cross-linked on the cell surface, resulting in the physiological effects of IgE-antigen interaction. Degranulation results in release of, among other substances, histamine, heparin, chemotactic factor for eosinophils and the leukotrienes, C4, D4 and E4, which cause prolonged constriction of bronchial smooth muscle cells. Hood, L. E. et al., *Immunology* (2nd ed.), pp. 460–462, The Benjamin/Cumming Publishing Co., Inc. (1984). These released substances are the mediators which result in allergic symptoms caused by combination of IgE with a specific allergen. Through them, the effects of an allergen are manifested. Such effects may be systemic or local in nature, depending on the route by which the antigen entered the body and the pattern of deposition of IgE and mast cells. Local manifestations generally occur on epithelial surfaces at the location at which the allergen entered the body. Systemic effects can include anaphylaxis (anaphylactic shock), which is the result of an IgE-basophil response to circulating (intravascular) antigen.

It has been estimated that there are approximately 10 million cat allergic individuals in the United States. Ohman, J. L. and Sundin, B., *Clin. Rev. Allergy,* 5:37–47 (1987). An allergen of particular concern for many people is the feline skin and salivary gland allergen of the domestic cat *Felis domesticus* allergen I (Fel d I), also referred to as allergen I, cat 1 and antigen 4. Fel d I has been described as an acidic non-covalently linked homodimer of approximately 39,000 molecular weight on size exclusion HPLC, and 17,000 under nonreducing conditions on gel electrophoresis. Chapman, M. D. et al., *J. Immunology,* 140(3):812–818 (1988). Chapman and co-workers also describe a single step procedure for the purification of Fel d I from crude house dust extract with a high Fel d I content (50 U/ml) using monoclonal antibody affinity chromatography. In addition, they determined the amino acid composition and partial amino acid sequence of Fel d I. Fel d I has also been described as a 35,000 molecular weight dimer of two noncovalently linked 18,000 molecular weight subunits, which occurs in three isoallergenic forms (pI 3.5 to 4.1). Ohman, J. L. et al., *J. Allergy Clin. Immunol.,* 52:231 (1973); Ohman, J. L. et al., *J. Immunol,* 113:1668 (1974); Leiterman, K. and Ohman, J. L., *J. Allergy Clin. Immunol.,* 74:147 (1984).

Exposure to cat allergen can occur as a result of exposure to the animal or contact with house dust which contains cat allergens. These allergens have been examined in saliva, skin scrapings, cat wash, serum, salivary glands, cat hair, cat dandruff and house dust.

Current desensitization therapy involves treatment with a complex, poorly-defined animal dander extract which often causes adverse effects in individuals to whom it is administered.

SUMMARY OF THE INVENTION

The present invention relates to proteins for use in desensitization treatment of cat-sensitive individuals which stimulate T cells from a cat allergic individual but which interact with human IgE to a lesser extent than affinity purified human T cell reactive feline protein (TRFP) also referred to herein as Fel d I, interacts with human IgE. The proteins of the present invention are referred to as modified human T cell reactive feline proteins (modified TRFP) also referred to herein as modified Fel d I, and are produced by a method which is also the subject of the present invention. The present invention further relates to methods of modifying cat allergens in order to reduce their IgE reactivity while retaining their ability to stimulate T cells and to modified cat allergens produced by the method.

Modified human T cell reactive feline proteins of the present invention can be administered to a cat sensitive or cat allergic individual in order to desensitize the individual. Their use for this purpose has advantages over presently-used desensitization agents because of their lessened IgE interaction, which means their administration is accompanied by fewer IgE-mediated adverse effects.

BRIEF DESCRIPTION OF THE DRAWINGS

FIGS. 2a and 2b depict two types of immunoblots with antibody binding patterns using untreated, KOH- (potassium hydroxide) treated TRFP and N-glycosidase-treated TRFP.

DETAILED DESCRIPTION OF THE INVENTION

Figure 1A:
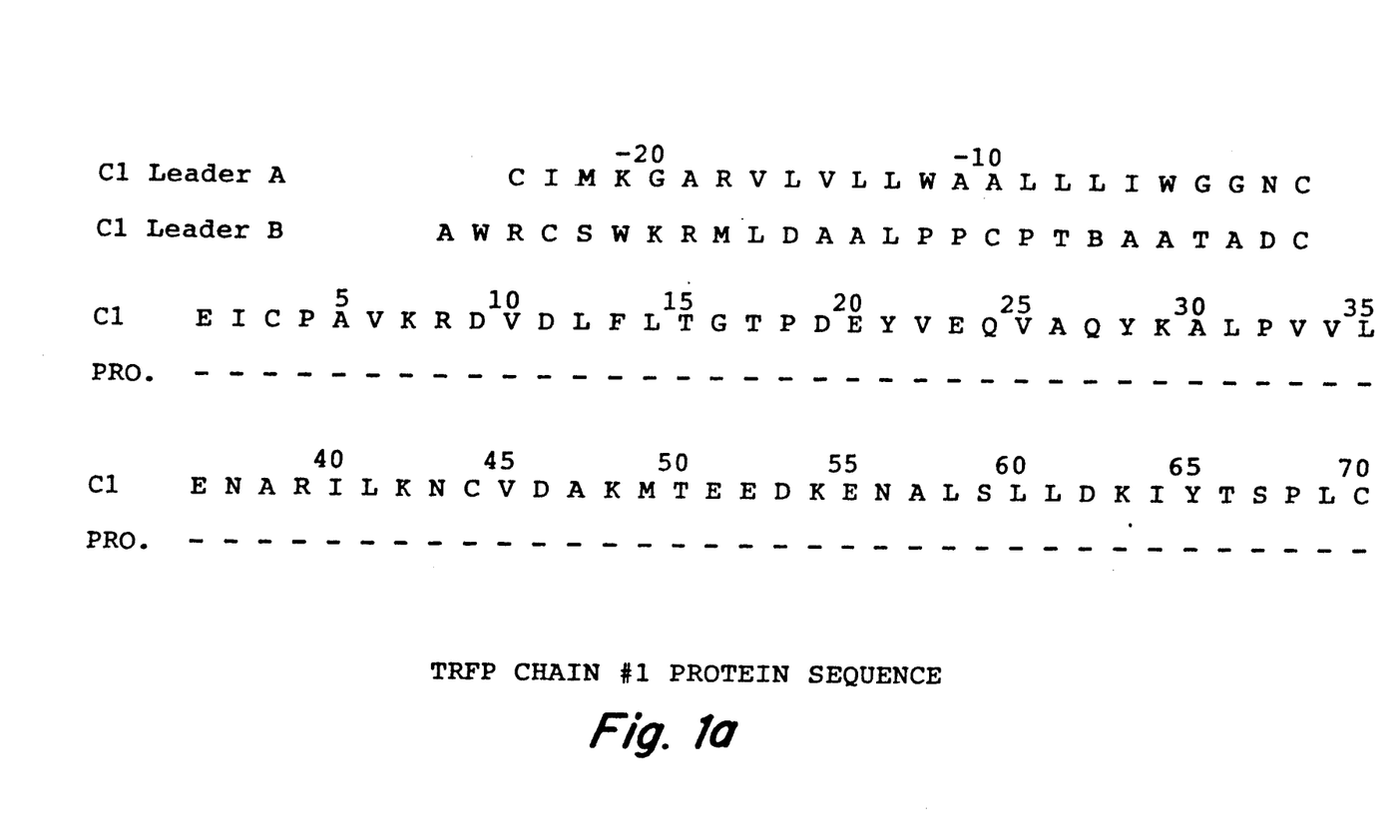
FIGS. 1a and 1b (together, FIG. 1) show the deduced amino acid sequence of TRFP chain 1 and chain 2 and the amino acid sequence of TRFP chain 1 and chain 2 determined by protein sequence analysis.
Figure 1B:
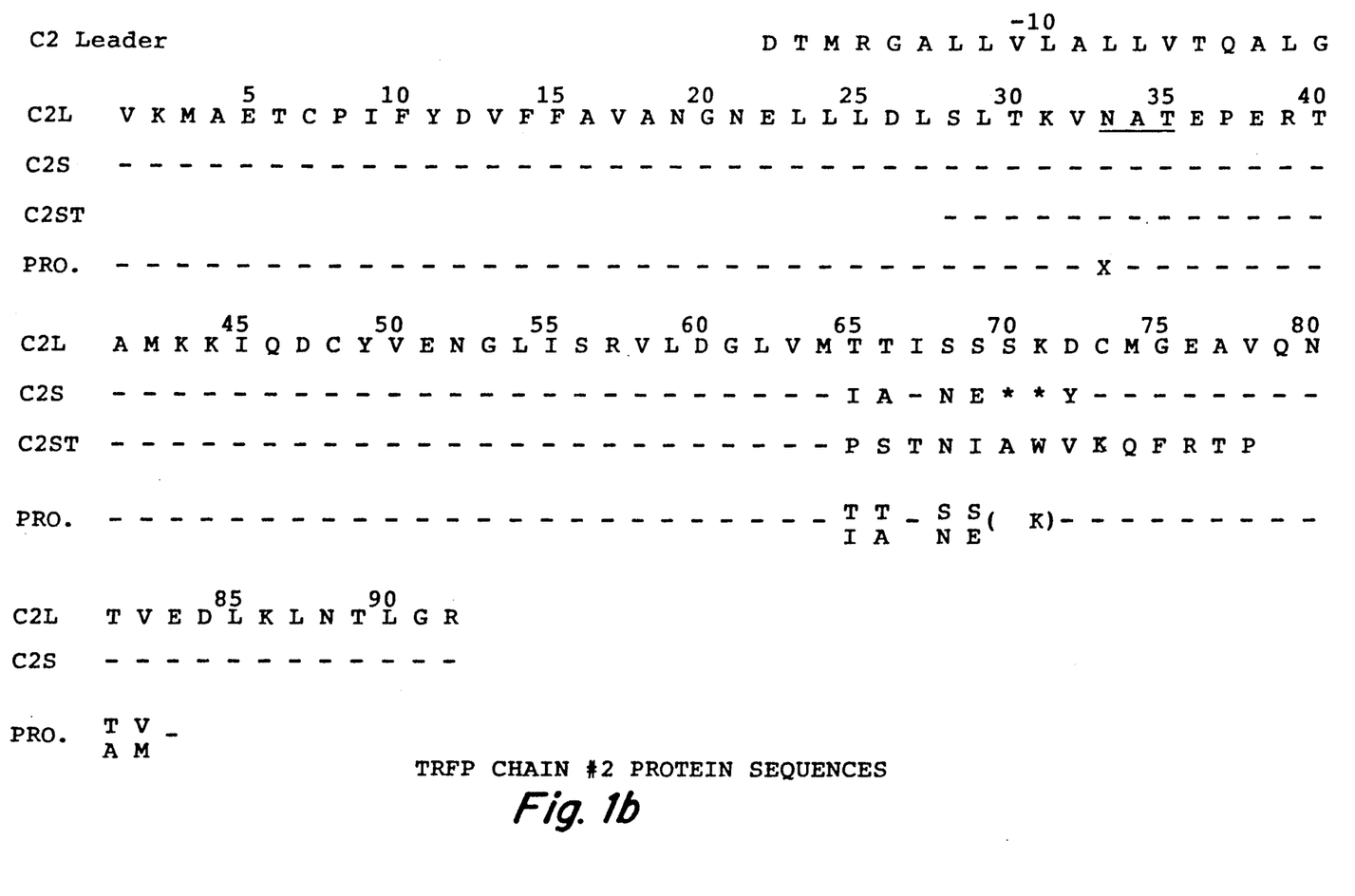

In order to improve desensitization therapy, a major cat dander allergen, which is a human T cell reactive feline protein, has been isolated by affinity purification from cat hair extract or vacuum cleaner bag house dust collected from homes with cats. The protein has been characterized by protein sequence analysis, cloned, and expressed in *E. coli*, as described in co-pending U.S. patent applications Ser. No. 07/431,565 Ser. No. 07/662,276, filed Nov. 3, 1989 and Feb. 28, 1991, respectively entitled "A Feline T Cell Reactive Cat Protein Isolated from House Dust and Uses Therefor". The teachings of these two applications are incorporated herein by reference. The T cell reactive feline protein, referred to as TRFP, has been shown to be a glycoprotein of approximately 40,000 M.W., which is composed of two covalently linked chains. The first chain (chain 1) is a 70 amino acid peptide. The second chain (chain 2) occurs either in a long form (92 amino acids) or in a short form (90 amino acids). The primary structure of these two chains is shown in FIG. 1 and represented in SEQ ID NO: 1-8. In addition, there is an N-linked carbohydrate structure attached to the amino acid Asn33 on chain 2 of TRFP. Moreover, it appears that the chains have an O-linked structure attached (possibly a carbohydrate), as evidenced by the fact that both chains can be modified by treatment with a mild base.

As described herein, the TRFP has been modified in such a manner that the resulting modified TRFP has reduced human IgE binding reactivity (i.e., binds with human IgE to a lesser extent than does unmodified affinity purified TRFP). In particular, modified TRFP has been produced by treating TRFP with mild base or alkali conditions, resulting in removal of some or all of the IgE reactive portions of the TRFP. The modified TRFP produced in this manner has been shown to have reduced ability to bind IgE from cat allergic individuals (relative to affinity purified TRFP) and to have substantially unaltered ability to stimulate T cells from cat allergic individuals (relative to affinity purified TRFP). As described further below, the IgE binding components of TRFP are apparently not N-linked carbohydrates, but appeared to be low molecular weight O-linked structures which may be carbohydrates, phosphate groups, acyl derivatives, phospholipid or other phosphodiester derivatives.

It is also possible that treatment with KOH can cause something other than removal of O-linked groups (e.g., destruction of the conformational epitope, deamidation), which could contribute to the lack of binding of the IgE binding components of TRFP. The IgE binding may be altered by deamidation or another type of reaction which changes amino acid side chains and/or the peptide backbone structure.

The modified TRFP of the present invention can be produced by mild alkali treatment, using any hydroxy base (e.g., potassium hydroxide (KOH), sodium hydroxide (NaOH), lithium hydroxide (LiOH)) or compounds (e.g., tertiary amines) which will produce hydroxide compounds. Treatment under mild alkali conditions is generally carried out at a pH of from about 12.0–14.0 and preferably at a pH of from about 12.5–13.5. Methods other than treatment with mild alkali can be used to generate the modified TRFP of the present invention. For example, modified TRFP having the IgE binding components removed can be produced by treating affinity purified TRFP with an enzyme, such as with O-glycanase, phosphatase, phospholipase and esterase, which enzymatically removes O-linked groups, such as carbohydrates, or chemical hydrolysis under strong acid conditions, such as with hydrogen fluoride, trifluoroacetic acid or trifluoromethane sulfonic acid treatment. Modified TRFP of the present invention can also be produced using recombinant DNA techniques. That is, once the alterations in the structure of the modified TRFP are known, it can be produced by introducing the DNA encoding the modified TRFP into an appropriate expression system that will generate the TRFP lacking the IgE binding portions. Alternatively, modified TRFP can be synthesized using chemical means. Based on the work described herein, cat allergens other than affinity purified TRFP can also be modified to remove corresponding O-linked structures believed to be responsible for IgE binding, while retaining their ability to stimulate T cells from cat allergic individuals. As used herein, the term modified TRFP includes proteins obtained by any of the methods described above (modification of TRFP, recombinant means and synthetic or chemical methods) which exhibit reduced human IgE binding reactivity and have substantially unaltered ability to stimulate T cells from cat allergic individuals (relative to affinity purified TRFP).

The following is a description of production and characterization of the modified TRFP of the present invention, production of other cat allergens (referred to as modified cat allergens) which stimulate T cells from cat allergic individuals and have reduced ability to bind IgE from cat allergic individuals, and use of modified TRFP or modified cat allergens to desensitize cat allergic individuals.

As described in co-pending U.S. patent application Ser. No. 07/431,565, affinity purified TRFP has been isolated. The deduced amino acid sequence of TRFP, chain 1 and chain 2, and the amino acid sequence of TRFP, chain 1 and chain 2, determined by protein sequence analysis, are shown in FIG. 1 and represented in SEQ ID NO: 1-8. Treatment of affinity purified TRFP with mild base has been carried out, as described in Example 1. This resulted in production of modified TRFP, which has been characterized through the combination of anti-peptide antisera, monoclonal antibodies and IgE immunoblot analysis. The TRFP specific IgE was obtained from plasma from cat allergic patients. Results demonstrated that the mild base treatment removed or altered component(s) of the affinity purified TRFP responsible for IgE binding. Results also strongly suggest that the vast majority of components responsible for IgE binding are not N-linked carbohydrates, are of low molecular weight and are O-linked moities (e.g., carbohydrates, phosphate groups, acyl derivatives, phospholipid or other phosphodiester derivatives). The mild base treatment did not, however, significantly alter T cell reactive moieties and the ability of the resulting modified TRFP to stimulate T cells from cat sensitive individuals is comparable to that of unmodified TRFP. SDS-polyacrylamide gel electrophoresis (SDS-PAGE) immunoblot analysis of the reaction products indicated that the allergenic structures of affinity purified TRFP can be O-linked carbohydrates of low molecular weight or other O-linked post-translational modification of the TRFP in the feline tissues. Sharon, N., "Complex Carbohydrates, Their Chemistry, Biosynthesis, and Functions" 65-83 Addison-Wesley Publishing Company, 1975.

Affinity purified antisera raised against peptides derived from the chain 1 protein sequence anti-Fel 2 (anti-Cl peptide 9-25) and anti-Fel 4 (anti-Cl peptide 37-55) or from the chain 2 protein sequence anti-Fel 18 (anti-C2 peptide 23-48) have been used to identify the protein backbone. In addition, five monoclonal antibodies (1G9, 6F9, 3E4, 2H4 and 10F7) that were generated against *Felis domesticus* allergen I, have been used to monitor the removal of the IgE binding post-translational moieties. All of these monoclonal antibodies show greatly reduced binding to the alkali treated cat allergen, indicating that they too are binding to the O-linked structures. This is in contrast to the pattern of binding demonstrated with the anti-peptide antisera. This fact affords the ability to use these antibodies to analyze the structure of the alkali sensitive components and relate any treatment regimen to IgE recognition of TRFP. There is an N-linked carbohydrate structure attached to the amino acid Aspargine (Asn) at position 33 on chain 2 of the TRFP. However, the N-linked carbohydrate structure is not related to the alkali sensitive modification upon which human IgE binding depends.

Mild Base Treatment of TRFP Removes Its IgE Binding Reactivity

Figure 2A:
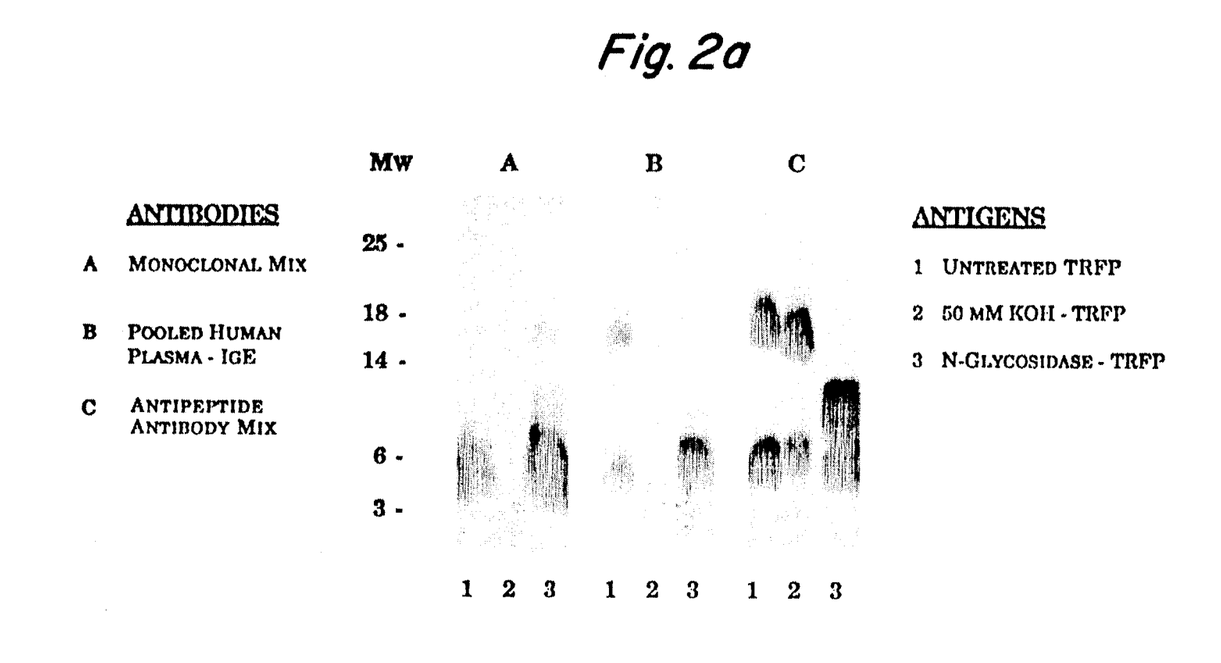
FIG. 2a shows three SDS-PAGE immunoblot sections, each with three different preparations of TRFP. Each section has been probed with distinct antisera; A- a mix of four monoclonal antibodies generated against TRFP, B- a combination of human plasma samples from cat allergic patients, C- a combination of four affinity purified rabbit antisera generated against specific peptides from TRFP amino acid sequence.
Figure 2B:
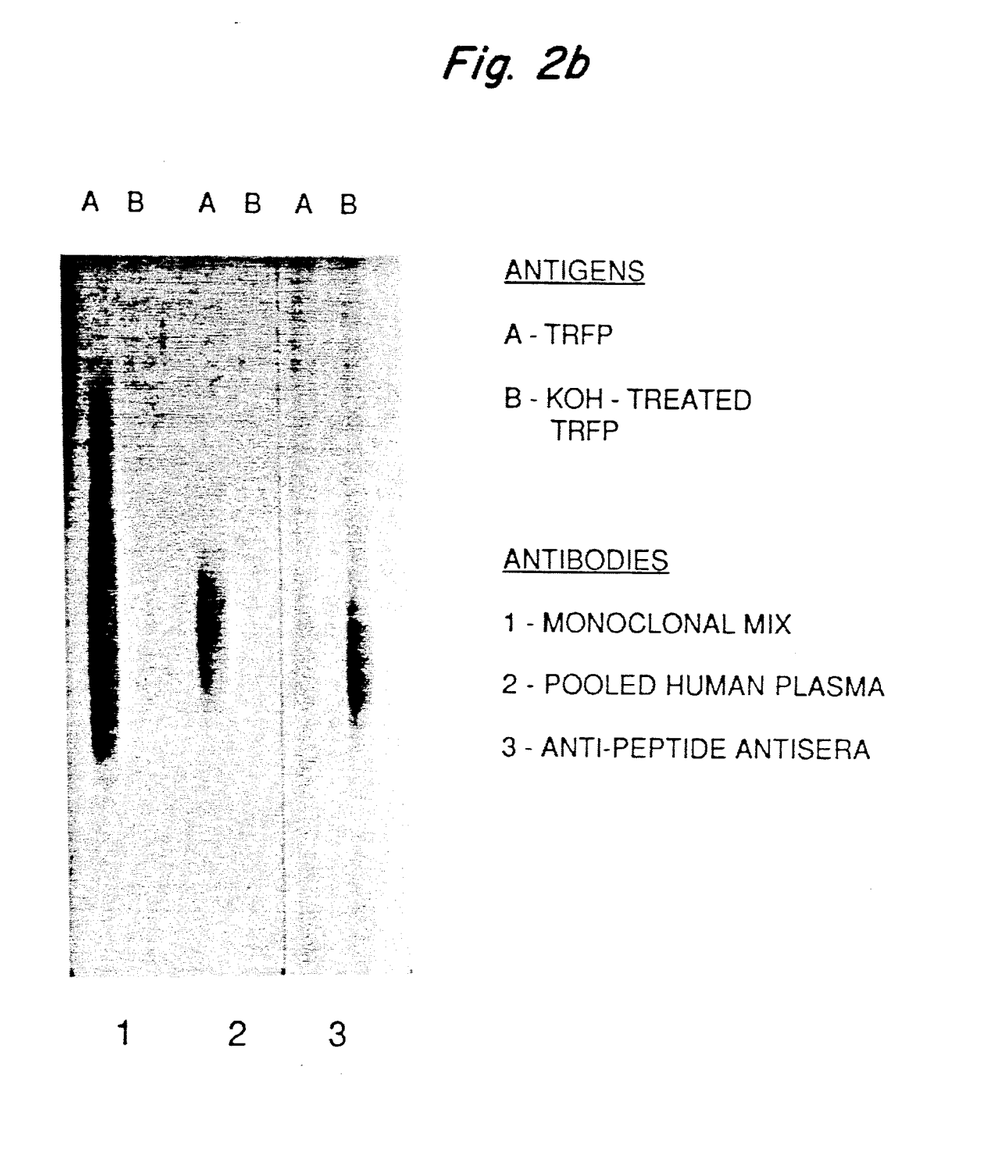
FIG. 2b is a set of six IEF sections of alternating untreated TRFP samples (1) and potassium hydroxide (KOH) treated TRFP samples (2) analyzed with the same antisera set as in panel IA, B and C.

As described in Example 1, affinity purified anti-peptide antisera raised against TRFP chain 1 and chain 2 have been used to identify the protein backbone before and after the dilute alkali treatment. The 3-6 kD band and 10-18 kD band on SDS-PAGE/Western immunoblot are chain 1 and chain 2 of TRFP, respectively (See FIG. 2a, Section C). These are described and shown in FIG. 8 of co-pending application entitled: "A Feline T Cell Reactive Cat Protein Isolated from House Dust and Uses Therefor," by Malcolm L. Gefter, Richard D. Garman, Julia L. Greenstein, Mei-chang Kuo, Bruce L. Rogers and Andrew W. Braver, PCT/US90/06548. Separately, both the mixture of monoclonal antibodies and the IgE from cat allergic patients bind to the two chains of TRFP as shown in FIG. 2a. Isoelectric focusing of TRFP followed by immunoblot analysis is performed in order to examine the antibody binding reactivity with intact TRFP. As described in Example 1, the monoclonal antibody mixture and IgE from cat allergic patients did not bind to the mild base treated TRFP (FIG. 2b).

The mild base treatment of TRFP had little effect on the protein backbone structure. That is, an average of about 10% of the Asn residues were deamidated or cleaved on the amino end. These minor chemical changes cannot account for the dramatic loss of antibody recognition of TRFP.

N-glycosylation was also shown not to be sensitive to dilute alkali treatment or the base-catalyzed beta-elimination which is likely to be the reaction mechanism involved. It has been shown that the N-linked carbohydrate can be removed by specific endoglycosidase, as shown by the fact that treatment of TRFP with N-glycosidase F(PNGase, Boehringer Mannheim) resulted in a decrease of the molecular weight of TRFP chain 2 by approximately 8 kD, as assayed by immunoblot methods. However, the antibody recognition of the cat allergen by monoclonal antibodies and cat allergic patient's IgE showed very little alteration following this N-glycosidase F treatment (FIGS. 2a and 2b).

Therefore, using the combination of anti-peptide antisera, monoclonal antibodies and cat allergic patient's IgE immunoblot analysis, it has been shown that mild base treatment removes the components responsible for IgE binding. Results of these assays show that the structures responsible for IgE binding are not N-linked carbohydrates. They also demonstrate that there is no significant molecular weight change after alkali treatment of either chain 1 or 2, revealing that the IgE binding components have low molecular weight. This latter finding indicates that the O-linked structures may be carbohydrates, phosphate groups, acyl derivatives, phospholipid or other phosphodiester derivatives.

Figure 3:
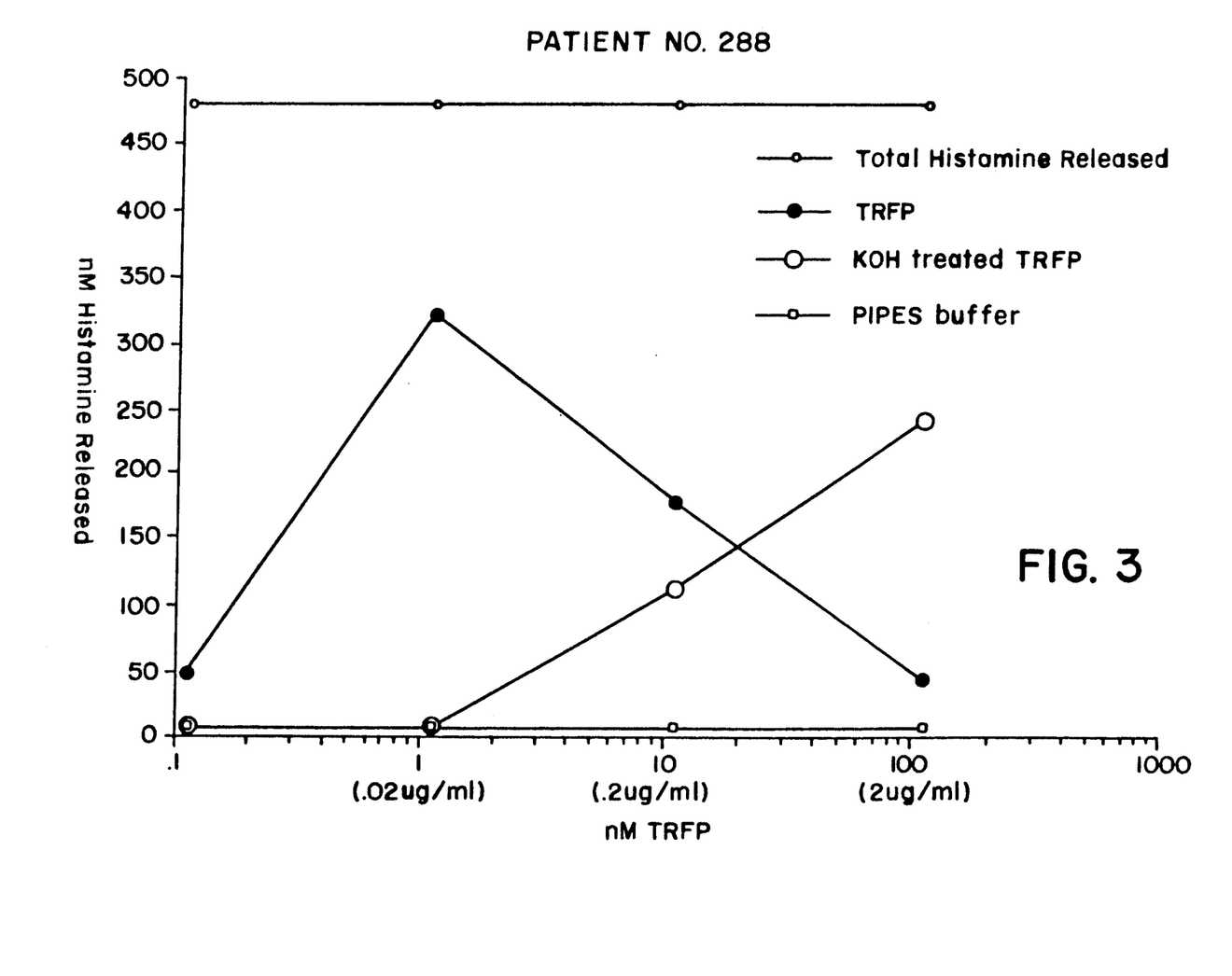
FIG. 3 is a graphic representation of results from a histamine release analysis using whole blood from a cat allergic patient. The treated and untreated TRFP were used at four concentrations ranging from 0.1 to 100 nM and histamine release from these treatments was compared to the total histamine level and to the buffer control.

It is also reasonable to expect that such alkali treated TRFP has reduced histamine releasing properties when compared to affinity purified (untreated) TRFP. As shown in FIG. 3, alkali treated TFRP showed greater than 95% reduction in its histamine releasing property in the plasma of one cat allergic individual. This reduced in vitro histamine releasing activity is a direct measure of the reduced allergenic potential of treated TRFP.

The removal of the IgE reactive portions of the TRFP molecule in the manner described herein did not result in removal of T cell reactive structures and, thus, the resulting modified TRFP is able to stimulate T cells, as is desired in a reagent to be used in desensitization therapy. The epitopes of TRFP recognized by cat allergic patients' T cells are made up of linear protein sequence. The modified TRFP, which has the correct T cell epitopes (as they occur in TRFP) but lacks IgE allergic reactivity is useful in desensitization of cat allergic individuals and has the advantage that adverse reactions resulting from IgE binding cannot occur. When modified TRFP is introduced into an individual during prophylaxis for cat dander allergy, there should be a change in the immune response such that the allergic symptoms diminish. Thus, exposure of cat allergic patients to KOH modified TRFP or TRFP modified by another means may tolerize or anergize appropriate T cell subpopulations so that they no longer respond to cat allergen(s) and do not participate in mounting an allergenic immune response to such exposure.

Alternative Methods of Removing the O-linked Non-Amino Acid Components

If the cat allergic patients' IgE binding epitopes are O-linked to the protein backbone, known techniques such as treatment with a strong acid (e.g., trifluoromethanelsulfonic acid, trifluoracetic acid, hydrofluoric acid), a redox agent (e.g., nitrous acid) or an enzyme (e.g., an endo- or an exoglycosidase, phosphatase, phospholipase, esterase), can be used for the removal of these structures.

Alternatively, TRFP chain 1 and chain 2 can be produced using recombinant techniques, as described herein. For example, they can be produced in *E. coli*, which lack the glycosylation enzymes of mammalian systems. This can be extended to any recombinant expression system which can produce the TRFP lacking the IgE binding components. Chemical synthetic methods may also be employed to generate the modified TRFP void of IgE binding.

Other modifications of the structure of TRFP are also possible. For example, using recombinant technology or chemical synthesis the O-glycosylation sites, either serine and/or threonine residues, can be substituted with other amino acid residues such as glycine or any other residue that does not have hydroxy functional groups to remove the sites for post-translational processing.

Uses of the Mild Base Treated T Cell Reactive Feline Protein (TRFP)

The material resulting from the work described herein, can be used in methods for treating and preventing cat allergy. In addition, the monoclonal or polyclonal antibodies which bind with these O-linked non-amino acid components can be used to identify the potential adverse effect of the desensitization therapeutic agent. Through use of the protein of the present invention, allergen preparations with very low IgE binding activity can be made and administered for therapeutic purposes (e.g., to modify the allergic response of a cat-sensitive individual to cat allergies). Such a protein or peptide (or modified version thereof, such as is described below) may, for example, modify B-cell response to cat allergen, T cell response to cat allergen or both responses.

Work by others has shown that high doses of allergens during immunotherapy treatment generally produce the best results (i.e., best symptom relief). However, many people are unable to tolerate large doses of allergens because of adverse IgE mediated reactions to the allergens.

The present invention enables the production of therapeutic treatments for cat allergic individuals which will possess similar or improved efficacy to that of current allergen immunotherapy without the adverse reactions normally associated with this form of therapy. Improved therapy could derive from the use of mild base or other chemically or enzymatically treated TRFP or peptide expression products of the TRFP genes identified herein or appropriate modifications (mutations) thereof.

Alternatively, the TRFP cDNAs defined herein, or portions thereof, can be expressed in appropriate systems to produce protein(s) with strong therapeutic activity, but greatly reduced ability to bind to IgE and therefore decreased adverse reactions.

The present invention will now be further illustrated by the following examples, which are not intended to be limiting in any way.

EXAMPLE 1

Treatment of TRFP to Remove IgE Binding

Figure 4:
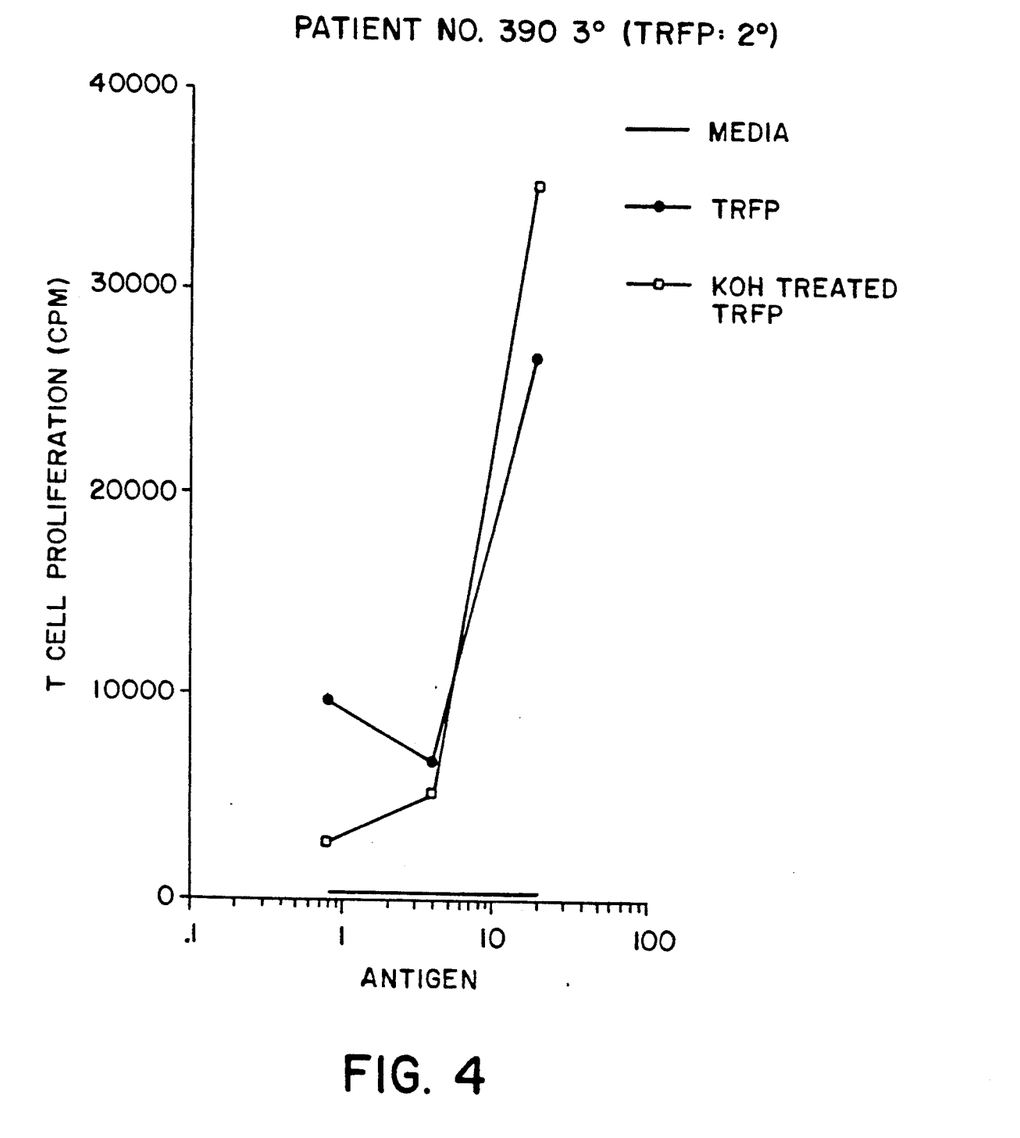
FIG. 4 is a graphic representation of the secondary T cell response of peripheral blood lymphocytes from a cat-sensitive individual stimulated with untreated TRFP and KOH-treated TRFP.

TRFP was affinity purified according to a published protocol. Chapman, M. D. et al., *Immunology*, 140(3):812-818 (1988). Affinity purified TRFP was incubated overnight (16 hours) under the following conditions; 1 milligram of TRFP in 1 milliliter of 1X PBS (phosphate buffered saline) with 50 microliters of 1M KOH (potassium phosphate) to give a final concentration of 50 mM KOH with a pH of 12.5. The incubation was carried out in a 1.5 ml polypropylene tube at room temperature (23° C.). The reaction was stopped by the addition of 50 microliters of Tris-HCl buffer, 2M, pH 7.5, which neutralizes the reaction. The sample was then dialyzed against three changes of 1X PBS and concentrated on Aquacide. This sample preparation was then examined by: a) immunoblot binding assays shown in FIG. 2, b) histamine release analysis as shown in FIG. 3, and also used in the T cell stimulation assay presented in FIG. 4. In all of these types of analyses the KOH-treated TRFP was compared to untreated TRFP. The N-glycosidase treatment of TRFP (lane 3, FIG. 2, panel 1) was performed to the enzyme manufacturer's specifications (Boehringer-Mannheim).

Immunoblotting

Protein preparations (5 μg/lane on all blots) were run on 18% acrylamide gels, transfers were then performed by electroblotting at 1.5 Amps for 1.5 hours onto nitrocellulose paper (Schleicher and Schuell, 0.1 microns) in a Hoeffer apparatus according to the protocol of Tobin et al. (1979). Proteins were rinsed in blot solution (25 mM Tris-HCL 7.5, 0.171M NaCl and 0.5 mls/liter Tween 20). Blots were then blocked for one hour in blocking solution (1% milk in blot solution). Blots were rinsed with blot solution and cut into sections. Human plasma pool used as a primary antibody source was diluted in blocking solution to 10% and preabsorbed for 1.5 hours with unused nitrocellulose (2 cm×15 cm). The prepared human plasma was then incubated overnight on an orbital shaker with the protein blot sections of interest. Following the first antibody incubation the blot sections were washed three times, fifteen minutes each wash in blot solution. The second antibody, specific for human IgE (biotinylated goat anti-human IgE, KPL Inc.), was diluted 1:2500 in blot solution and the incubation proceeded for two hours. Excess second antibody was subsequently removed by three 15 minute washings with blot solution. $^{125}$I Iodinated streptavidin (Amersham) was diluted 1:2500 in blot solution and incubated with blots for 1 hour, at 2 uCi incubation. Blot sections were then washed with blot solution until the detectable radioactivity in the waste solution decreased to background levels. The blot sections were then wrapped in saran wrap and exposed to film with a cronex intensifying screen at −80° C. For use as first antibody preparations the monoclonal mix was used at a 1:1000 dilution and the antipeptide mix at a 1:2000 dilution in blot solution.

IEF Gels for Immunoblotting

IEF gels, at 7.5% acrylamide, were performed in a Hoefer SE 600 series vertical slab gel unit. Glass plates were washed, silinized and assembled using 1.5 mm spacers. The following compounds were mixed and degassed for 5 minutes: 42.4 mls H$_2$O, 7.2 mls glycerol, 18 mls 30% Acrylamide-0.8% bis-Acrylamide, 4.5 mls Pharmalyte (Pharmacia, Inc.) pH 2.5-5. Prior to pouring the gel 0.250 mls of 10% ammonium persulfate (APS) and 0.12 mls of N,N,N,N-tetramethylethyl-diamine (TEMED) were then added to the solution. The gels were allowed to polymerize overnight at 4° C. The catholyte and anolyte used were 0.02M NaOH and 0.02M acetic acid respectively. Gels were prerun for 30 minutes at 13 watts. The TRFP preparation was diluted in sample buffer (395 μl H$_2$O, 75 μl glycerol and 30 μl Ampholytes 3.5-10.0) and loaded at a concentration of 10 μg per lane. Gels were run for 4-4.5 hours at 13 watts until constant voltage was reached.

IEF Immunoblotting

Proteins from IEF gels were transferred onto nitrocellulose under the same conditions as were the proteins from SDS PAGE gels, with the following exceptions:

IEF gels were allowed to equilibrate in transfer buffer for 5-15 minutes. Transfers were done for 1.5 hours at 1.5 amps.

The SDS-PAGE immunoblot data shown in FIG. 2a shows antibody binding to the untreated TRFP with all three distinct antibody preparations (lanes 1, sections A, B, and C). The pooled human plasma and the antipeptide antisera show clear binding to both chains of TRFP. On this representative blot from a 18% acrylamide gel both chains appear as a smear; chain 1 is 3-6 kD in size and chain 2 is 14-18 kD in size. The chain identification in relation to these two bands is supported by sequence determination and antipeptide antisera binding patterns. The binding pattern of the monoclonal antibody mix (the four monoclonal antibodies are termed; 1G9, 6F9, 3E4 and 10F7) shows a weak signal to the chain 2 band and strong signal from chain 1.

Lanes 2 in the three sections of FIG. 2a, show the binding patterns of the three antibody preparations to 50 mM KOH treated TRFP. The only positive signal of binding is on Section C using the antipeptide antisera. The alkali treatment has destroyed the binding sites for both the monoclonal antibodies and the human pooled plasma IgE. The pattern shown in lane 3 demonstrates binding by all the antibody preparations even though the N-glycosidase treatment reduced the apparent molecular weight of chain 2 (which contains the N-linked carbohydrate) by approximately 8 kD.

FIG. 2b shows the binding pattern of these same antisera (as used in FIG. 2a) on immunoblot sections from an IEF gel of untreated and 50 mM KOH treated TRFP. Lanes 1 on all three antibody sets is untreated TRFP and lane 2 strips show the alkali treated samples of TRFP. IEF separated TRFP protein is always a smear, however, the antipeptide binding shows no signal on the untreated preparation but strong binding is present with both the monoclonal antibodies and human IgE. The 50 mM KOH treated TRFP binding results are just the opposite. There is no recognition of this material by the IgE antibodies or the mouse monoclonal antibody mixture. The pattern of binding by the antipeptide antisera on the alkali treated sample is also a smear showing the distribution of electric charge on the molecule both before and after KOH treatment.

Histamine Release Analysis

The assay is based on the detection of an acylated derivative of histamine using a specific monoclonal antibody (Morel, A. M. and Delaage, M. A. ; 1988, *J. Allergy Clin. Immunol.* 82:646-654). The reagents for this radioimmunoassay are sold as a kit by Amac Inc.

Whole haeparinized blood was drawn from a cat allergic patient, #288, and used for the histamine release assay shown in FIG. 3. The antigens, untreated and KOH treated TRFP, were diluted to 2× concentration in −1× pipes buffer with 0.25 mls in each 1.5 ml polypropylene tube. The same volume of blood, 0.25 mls, was added to each tube and the reactions were started by inversion. The buffer control consisted of whole blood and buffer with no added antigen. The release reactions were then carried out at 37° C. for 30 minutes. After this incubation the tubes were centrifuged at 1500 RPM for 3 minutes and the supernatants were removed and diluted 1:4 for the acylation reactions. For the total histamine value 0.1 mls of blood was boiled in a total volume of 1.0 ml with 1× pipes buffer. This sample was spun at 13000 RPM for 3 minutes and the supernatants was removed for analysis. The graphed results from this analysis set are shown in FIG. 3. Approximately 100 times more KOH treated TRFP is required to get the same level of histamine release given by the untreated TRFP sample.

EXAMPLE 2

Trifluoromethanesulfonic Acid Treatment of TRFP

A dried affinity purified TRFP sample (1-20 mg) was stirred in 1 ml of anisole/anhydrous trifluoromethanesulfonic acid (TFMSA) at a 1:2 ratio for 4-5 hrs. at 0° C. The protein solution was diluted with 2 ml of cold diethyl ether (−70° C.).

Three ml of 50% aqueous pyridine was then slowly added and the temperature was kept below 5° C. Large amounts of pyridinium salt of TFMSA were formed, which redissolve at room temperature. The ether phase was removed after the ether and aqueous phase separated. The remaining aqueous phase was dialyzed extensively against pyridinium acetate buffer (pH 5.5). The protein was frozen and lyophilized for storage. This procedure should remove O-linked residues, but retain the N-linked residues (e.g., the N-glycosidically linked N-acetylglucosamine) (Glassman, J. N. S. Todd, C. W. and Shively, J. E. (1978) *Biochem. Biophys. Res. Comm.* 85:209-216. The TFMSA treated TRFP has lost its monoclonal antibody binding reactivity when it is examined with monoclonal antibody, 6F9, on SDS-PAGE/Western immunoblot.

EXAMPLE 3

The Human T Cell Response Is Similar with Untreated and Alkali Treated TRFP

Peripheral blood mononuclear cells (PBMC) were purified from 60 ml of heparinized blood from a cat allergic patient (#390). 10 mL of PBMC from patient #390 at 10⁶/ml were cultured at 37° C. for 7 days in the presence of 5 micrograms purified TRFP/ml RPMI-1640 supplemented with 5% pooled human AB serum. Viable cells were purified by Ficoll-Hypaque centrifugation and cultured for three weeks at 5 units recombinant human IL-2/ml and 5 units recombinant human IL-4/ml. The resting T cells were then restimulated (secondary) with one of the following preparations: untreated purified TRFP or 0.5M KOH treated TRFP at 20, 4, or 0.8 μg/ml, or with media alone containing no added antigen (See FIG. 4).

These secondary stimulations were done in a 96-well round bottom assay plate in a volume of 200 microliters with $2 \times 10^5$/ml T cells and $5 \times 10^5$/ml x-irradiated (3500 RAD) autologous PMBC for three days. Each well then received 1 microCurie tritiated (methyl)-thymidine for 16 hours. The counts incorporated were collected onto glass fiber filters and processed for liquid scintillation counting. The human T cell response was shown to be similar with untreated and alkali treated TRFP.

EQUIVALENTS

Those skilled in the art will recognize, or be able to ascertain using no more than routine experimentation, many equivalents to the specific embodiments of the invention described specifically herein. Such equivalents are intended to be encompassed in the scope of the following claims.

We claim:

1. A modified Fel d I, substantially free of other cat proteins, which is capable of stimulating T cells from a cat allergic individual and which interacts with human immunoglobulin E from a cat allergic individual to a lesser extent than does unmodified, affinity purified Fel d I, said modified Fel d I prepared by treating purified Fel d I with mild alkali.

2. A modified Fel d I according to claim 1, prepared by treating affinity purified Fel d I with alkali at a pH of from about 12.0 to 14.0.

3. A modified Fel d I according to claim 1, prepared by treating affinity purified Fel d I with a base selected from the group consisting of NaOH, KOH, LiOH and tertiary amines at a pH of from about 12.0 to 14.0.

4. A modified Fel d I according to claim 1, prepared by incubating affinity purified Fel d I with 50 mM KOH, pH 12.5–13.5, at room temperature.

5. A method for producing a modified Fel d I which is capable of stimulating T cells from a cat allergic individual and which interacts with human immunoglobulin E from a cat allergic individual to a lesser extent than does unmodified, affinity purified Fel d I, comprising the step of treating purified Fel d I with mild alkali.

6. The method of claim 5 wherein the purified Fel d I is treated with mild alkali at a pH of from about 12.5 to about 13.5.

7. The method of claim 6 wherein the mild alkali is selected from the group consisting of: potassium hydroxide, sodium hydroxide, lithium hydroxide and tertiary amines.

8. Modified Fel d I produced by the method of claim 6.

9. A method for reducing the extent to which purified Fel d I interacts with human immunoglobulin E from a cat allergic individual without substantially reducing its capability to stimulate human T cells, comprising contacting purified Fel d I with mild alkali at a pH of about 12.0 to 14.0.

10. The method according to claim 9 wherein the mild alkali is selected from the group consisting of: potassium hydroxide, sodium hydroxide, lithium hydroxide and tertiary amines.

11. The method according to claim 9 wherein the mild alkali is potassium hydroxide and the pH is from about 12.5 to 13.5.

* * * * *

UNITED STATES PATENT AND TRADEMARK OFFICE
CERTIFICATE OF CORRECTION

PATENT NO. : 5,328,991
DATED : Jul. 12, 1994
INVENTOR(S) : Mei-chang Kuo and Julian Bond

It is certified that error appears in the above-indentified patent and that said Letters Patent is hereby corrected as shown below:

On the title page:

[75] Inventor:   Mei-chang Kuo, Winchester, Mass. and
  Julian Bond, Weymouth, Mass.

Signed and Sealed this

Fifteenth Day of November, 1994

Attest:

BRUCE LEHMAN

Attesting Officer    Commissioner of Patents and Trademarks

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 94 amino acids
        ( B ) TYPE: amino acid
        ( D ) TOPOLOGY: linear     ( i i ) MOLECULE TYPE: peptide     ( v ) FRAGMENT TYPE: internal     ( x i ) SEQUENCE DESCRIPTION: SEQ ID NO:1:

```
Cys Ile Met Lys Gly Ala Arg Val Leu Val Leu Leu Trp Ala Ala Leu
1               5                   10                  15

Leu Leu Ile Trp Gly Gly Asn Cys Glu Ile Cys Pro Ala Val Lys Arg
            20                  25                  30

Asp Val Asp Leu Phe Leu Thr Gly Thr Pro Asp Glu Tyr Val Glu Gln
        35                  40                  45

Val Ala Gln Tyr Lys Ala Leu Pro Val Val Leu Glu Asn Ala Arg Ile
    50                  55                  60

Leu Lys Asn Cys Val Asp Ala Lys Met Thr Glu Glu Asp Lys Glu Asn
65                  70                  75                  80

Ala Leu Ser Leu Leu Asp Lys Ile Tyr Thr Ser Pro Leu Cys
                85                  90
```

( 2 ) INFORMATION FOR SEQ ID NO:2:

( i ) SEQUENCE CHARACTERISTICS:
        ( A ) LENGTH: 96 amino acids
        ( B ) TYPE: amino acid
        ( D ) TOPOLOGY: linear     ( i i ) MOLECULE TYPE: peptide     ( v ) FRAGMENT TYPE: internal     ( x i ) SEQUENCE DESCRIPTION: SEQ ID NO:2:

```
Ala Trp Arg Cys Ser Trp Lys Arg Met Leu Asp Ala Ala Leu Pro Pro
1               5                   10                  15

Cys Pro Thr Asx Ala Ala Thr Ala Asp Cys Glu Ile Cys Pro Ala Val
            20                  25                  30

Lys Arg Asp Val Asp Leu Phe Leu Thr Gly Thr Pro Asp Glu Tyr Val
        35                  40                  45

Glu Gln Val Ala Gln Tyr Lys Ala Leu Pro Val Val Leu Glu Asn Ala
    50                  55                  60

Arg Ile Leu Lys Asn Cys Val Asp Ala Lys Met Thr Glu Glu Asp Lys
65                  70                  75                  80

Glu Asn Ala Leu Ser Leu Leu Asp Lys Ile Tyr Thr Ser Pro Leu Cys
                85                  90                  95
```

( 2 ) INFORMATION FOR SEQ ID NO:3:

( i ) SEQUENCE CHARACTERISTICS:
        ( A ) LENGTH: 70 amino acids
        ( B ) TYPE: amino acid
        ( D ) TOPOLOGY: linear     ( i i ) MOLECULE TYPE: peptide     ( v ) FRAGMENT TYPE: internal ( x i ) SEQUENCE DESCRIPTION: SEQ ID NO:3:

Glu Ile Cys Pro Ala Val Lys Arg Asp Val Asp Leu Phe Leu Thr Gly
1               5                   10                  15

Thr Pro Asp Glu Tyr Val Glu Gln Val Ala Gln Tyr Lys Ala Leu Pro
            20                  25                  30

Val Val Leu Glu Asn Ala Arg Ile Leu Lys Asn Cys Val Asp Ala Lys
            35                  40                  45

Met Thr Glu Glu Asp Lys Glu Asn Ala Leu Ser Leu Leu Asp Lys Ile
        50                  55                  60

Tyr Thr Ser Pro Leu Cys
65                  70

( 2 ) INFORMATION FOR SEQ ID NO:4:

( i ) SEQUENCE CHARACTERISTICS:
    ( A ) LENGTH: 111 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:4:

Asp Thr Met Arg Gly Ala Leu Leu Val Leu Ala Leu Leu Val Thr Gln
1               5                   10                  15

Ala Leu Gly Val Lys Met Ala Glu Thr Cys Pro Ile Phe Tyr Asp Val
            20                  25                  30

Phe Phe Ala Val Ala Asn Gly Asn Glu Leu Leu Leu Asp Leu Ser Leu
            35                  40                  45

Thr Lys Val Asn Ala Thr Glu Pro Glu Arg Thr Ala Met Lys Lys Ile
        50                  55                  60

Gln Asp Cys Tyr Val Glu Asn Gly Leu Ile Ser Arg Val Leu Asp Gly
65                  70                  75                  80

Leu Val Met Thr Thr Ile Ser Ser Ser Lys Asp Cys Met Gly Glu Ala
                85                  90                  95

Val Gln Asn Thr Val Glu Asp Leu Lys Leu Asn Thr Leu Gly Arg
                100                 105                 110

( 2 ) INFORMATION FOR SEQ ID NO:5:

( i ) SEQUENCE CHARACTERISTICS:
    ( A ) LENGTH: 109 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:5:

Asp Thr Met Arg Gly Ala Leu Leu Val Leu Ala Leu Leu Val Thr Gln
1               5                   10                  15

Ala Leu Gly Val Lys Met Ala Glu Thr Cys Pro Ile Phe Tyr Asp Val
            20                  25                  30

Phe Phe Ala Val Ala Asn Gly Asn Glu Leu Leu Leu Asp Leu Ser Leu
            35                  40                  45

Thr Lys Val Asn Ala Thr Glu Pro Glu Arg Thr Ala Met Lys Lys Ile
        50                  55                  60

Gln Asp Cys Tyr Val Glu Asn Gly Leu Ile Ser Arg Val Leu Asp Gly
65                  70                  75                  80

```
              Leu  Val  Met  Ile  Ala  Ile  Asn  Glu  Tyr  Cys  Met  Gly  Glu  Ala  Val  Gln
                                  85                       90                      95

Asn  Thr  Val  Glu  Asp  Leu  Lys  Leu  Asn  Thr  Leu  Gly  Arg
                                 100                      105
```

( 2 ) INFORMATION FOR SEQ ID NO:6:

( i ) SEQUENCE CHARACTERISTICS:
        ( A ) LENGTH: 51 amino acids
        ( B ) TYPE: amino acid
        ( D ) TOPOLOGY: linear     ( i i ) MOLECULE TYPE: peptide     ( v ) FRAGMENT TYPE: internal     ( x i ) SEQUENCE DESCRIPTION: SEQ ID NO:6:

```
              Ser  Leu  Thr  Lys  Val  Asn  Ala  Thr  Glu  Pro  Glu  Arg  Thr  Ala  Met  Lys
              1                  5                        10                      15

Lys  Ile  Gln  Asp  Cys  Tyr  Val  Glu  Asn  Gly  Leu  Ile  Ser  Arg  Val  Leu
                                  20                       25                      30

Asp  Gly  Leu  Val  Met  Pro  Ser  Thr  Asn  Ile  Ala  Trp  Val  Lys  Gln  Phe
                            35                       40                      45

Arg  Thr  Pro
                       50
```

( 2 ) INFORMATION FOR SEQ ID NO:7:

( i ) SEQUENCE CHARACTERISTICS:
        ( A ) LENGTH: 83 amino acids
        ( B ) TYPE: amino acid
        ( D ) TOPOLOGY: linear     ( i i ) MOLECULE TYPE: peptide     ( v ) FRAGMENT TYPE: internal     ( x i ) SEQUENCE DESCRIPTION: SEQ ID NO:7:

```
              Val  Lys  Met  Ala  Glu  Thr  Cys  Pro  Ile  Phe  Tyr  Asp  Val  Phe  Phe  Ala
              1                  5                        10                      15

Val  Ala  Asn  Gly  Asn  Glu  Leu  Leu  Leu  Asp  Leu  Ser  Leu  Thr  Lys  Val
                                  20                       25                      30

Xaa  Ala  Thr  Glu  Pro  Glu  Arg  Thr  Ala  Met  Lys  Lys  Ile  Gln  Asp  Cys
                            35                       40                      45

Tyr  Val  Glu  Asn  Gly  Leu  Ile  Ser  Arg  Val  Leu  Asp  Gly  Leu  Val  Met
                       50                       55                      60

Thr  Thr  Ile  Ser  Ser  Xaa  Lys  Asp  Cys  Met  Gly  Glu  Ala  Val  Gln  Asn
              65                       70                      75                           80

Thr  Val  Glu
```

( 2 ) INFORMATION FOR SEQ ID NO:8:

( i ) SEQUENCE CHARACTERISTICS:
        ( A ) LENGTH: 83 amino acids
        ( B ) TYPE: amino acid
        ( D ) TOPOLOGY: linear     ( i i ) MOLECULE TYPE: peptide     ( v ) FRAGMENT TYPE: internal     ( x i ) SEQUENCE DESCRIPTION: SEQ ID NO:8:

```
              Val  Lys  Met  Ala  Glu  Thr  Cys  Pro  Ile  Phe  Tyr  Asp  Val  Phe  Phe  Ala
              1                  5                        10                      15

Val  Ala  Asn  Gly  Asn  Glu  Leu  Leu  Leu  Asp  Leu  Ser  Leu  Thr  Lys  Val
                                  20                       25                      30
```

| Xaa | Ala | Thr | Glu | Pro | Glu | Arg | Thr | Ala | Met | Lys | Lys | Ile | Gln | Asp | Cys |
|     |     | 35  |     |     |     |     | 40  |     |     |     |     | 45  |     |     |     |

| Tyr | Val | Glu | Asn | Gly | Leu | Ile | Ser | Arg | Val | Leu | Asp | Gly | Leu | Val | Met |
|     | 50  |     |     |     |     | 55  |     |     |     |     | 60  |     |     |     |     |

| Ile | Ala | Ile | Asn | Glu | Xaa | Lys | Asp | Cys | Met | Gly | Glu | Ala | Val | Gln | Asn |
| 65  |     |     |     |     | 70  |     |     |     |     | 75  |     |     |     |     | 80  |

| Ala | Met | Glu |